(12) United States Patent
Byun et al.

(10) Patent No.: US 11,621,421 B2
(45) Date of Patent: Apr. 4, 2023

(54) ORGANIC POSITIVE ELECTRODE ACTIVE MATERIAL FOR AQUEOUS REDOX FLOW BATTERY

(71) Applicant: LG CHEM, LTD., Seoul (KR)

(72) Inventors: Sujin Byun, Daejeon (KR); Sungyeon Kim, Daejeon (KR); Bong Hyun Jeong, Daejeon (KR); Tae Geun Noh, Daejeon (KR); Jeongbae Lee, Daejeon (KR); Esder Kang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 17/369,558

(22) Filed: Jul. 7, 2021

(65) Prior Publication Data

US 2021/0336264 A1 Oct. 28, 2021

Related U.S. Application Data

(62) Division of application No. 16/308,092, filed as application No. PCT/KR2017/010427 on Sep. 22, 2017, now abandoned.

(30) Foreign Application Priority Data

Sep. 22, 2016 (KR) .......................... 10-2016-0121644

(51) Int. Cl.
*H01M 4/60* (2006.01)
*H01M 8/18* (2006.01)
(Continued)

(52) U.S. Cl.
CPC ............. *H01M 4/60* (2013.01); *C07C 205/22* (2013.01); *C07C 215/76* (2013.01);
(Continued)

(58) Field of Classification Search
CPC ........... H01M 8/188; H01M 8/08; H01M 8/20
See application file for complete search history.

(56) References Cited

U.S. PATENT DOCUMENTS 3,338,806 A * 8/1967 Harwood .................. C25B 3/25
205/437
4,636,286 A * 1/1987 DeLue ...................... C25B 3/00
205/413
(Continued)

FOREIGN PATENT DOCUMENTS

AR 10-2016-0035338 A 3/2016
CN 1886811 A 12/2006
(Continued)

OTHER PUBLICATIONS

Shen, Jinyou, et al. "Bioelectrochemical system for recalcitrant p-nitrophenol removal." Journal of hazardous materials 209 (2012): 516-519. (Year: 2012).*

(Continued)

*Primary Examiner* — Ula C Ruddock
*Assistant Examiner* — Amanda Rosenbaum
(74) *Attorney, Agent, or Firm* — Birch, Stewart, Kolasch & Birch, LLP

(57) ABSTRACT

An organic positive electrode active material for aqueous redox flow batteries, and more particularly, to technology of applying an organic positive electrode active material to make up for the drawbacks of conventional aqueous redox flow batteries. An aqueous redox flow battery to which a particular positive electrode active material is applied has no problems regarding metal deposition, and can also be useful in realizing a high energy density because the positive electrode active material may be used at high concentration due to an increase in solubility in a solvent, attaining a high working voltage, and enhancing energy efficiency. Also, the
(Continued)

aqueous redox flow battery has excellent economic feasibility because an expensive organic electrolyte is not used.

3 Claims, 2 Drawing Sheets

(51) Int. Cl.
  *H01M 8/08*   (2016.01)
  *C07C 205/22*   (2006.01)
  *C07C 215/76*   (2006.01)
  *H01M 8/20*   (2006.01)
  *H01M 4/36*   (2006.01)
  *H01M 4/02*   (2006.01)

(52) U.S. Cl.
  CPC ............. *H01M 4/368* (2013.01); *H01M 8/08* (2013.01); *H01M 8/188* (2013.01); *H01M 2004/028* (2013.01); *Y02E 60/50* (2013.01)

(56) References Cited

U.S. PATENT DOCUMENTS

| | | | |
|---|---|---|---|
| 5,066,369 A * | 11/1991 | Yun | C25B 3/25 205/437 |
| 6,143,443 A | 11/2000 | Kazacos et al. | |
| 6,497,973 B1 * | 12/2002 | Amendola | H01M 4/5825 205/345 |
| 9,300,000 B2 | 3/2016 | Jansen et al. | |
| 2007/0121276 A1 | 5/2007 | Uzawa et al. | |
| 2013/0045428 A1 | 2/2013 | Visco et al. | |
| 2014/0170460 A1 * | 6/2014 | Park | H01M 8/188 429/105 |
| 2014/0178735 A1 | 6/2014 | Wang et al. | |
| 2014/0302370 A1 | 10/2014 | Woodford | |
| 2014/0370403 A1 | 12/2014 | Narayan et al. | |
| 2015/0140471 A1 * | 5/2015 | Dong | H01M 8/08 429/498 |
| 2015/0236543 A1 | 8/2015 | Brushett et al. | |
| 2016/0043423 A1 | 2/2016 | Huskinson et al. | |
| 2016/0093449 A1 * | 3/2016 | Yoon | H01G 11/32 252/182.1 |
| 2016/0233536 A1 | 8/2016 | Oh et al. | |

FOREIGN PATENT DOCUMENTS

| | | |
|---|---|---|
| JP | 2013-232434 A | 11/2013 |
| JP | 2014-127358 A | 7/2014 |
| JP | 2015-529941 A | 10/2015 |
| JP | 2016-162529 A | 9/2016 |
| KR | 10-2014-0071603 A | 6/2014 |
| KR | 10-1596218 B1 | 2/2016 |
| KR | 10-1600141 B1 | 3/2016 |
| WO | WO 2014/018495 A2 | 1/2014 |
| WO | WO 2015/048550 A1 | 4/2015 |
| WO | WO 2016/086163 A1 | 6/2018 |

OTHER PUBLICATIONS

Steenken, S., and P. Neta. "One-electron redox potentials of phenols. Hydroxy- and aminophenols and related compounds of biological interest." The Journal of Physical Chemistry 86.18 (1982): 3661-3667. (Year: 1982).*

Chinese Office Action and Search Report for Chinese Application No. 201780040304.2, dated Jan. 21, 2021, with English translation of the Office Action.

Duan et al., "Study on Electrochemical Oxidation of 4-Chlorophenol on a Vitreous Carbon Electrode Using Cyclic Voltammetry", Electrochimica Acta, vol. 94, Feb. 7, 2013, XP028997923, pp. 192-197.

Extended European Search Report dated Jul. 1, 2019, for European Application No. 17853446.7.

International Search Report (PCT/ISA/210) issued in PCT/KR2017/010427, dated May 21, 2018.

Kazacos, et al., "Vanadium redox cell electrolyte optimization studies", Journal of Applied Electrochemistry, 1990, vol. 20, pp. 463-467.

Kumar et al., "Performance Characteristics of Magnesium/Para-Nitrophenol Cells in 2:1 Magnesium Electrolytes", Journal of the Electrochemical Society, vol. 140, No. 11, Nov. 1, 1993, XP000424482, pp. 3087-3089.

Senthilkumar et al., "Redox Additive/active Electrolytes: a Novel Approach to Enhance the Performance of Supercapacitors", J. Materials Chemistry A, 2013, vol. 1, pp. 12386-12394. See p. 12389.

Winsberg et al., "Redox-Flow Batteries: From Metals to Organic Redox-Active Materials", Angew Chem. Int. Ed, Nov. 7, 2016., vol. 56, pp. 686-711. See pp. 693-704.

Xu et al., "Novel Organic Redox Flow Batteries Using Soluble Quinonoid Compounds as Positive Materials", WNWEC 2009, IEEE, 2009, DOI: 10.1109/WNWEC.2009.5335870 (inner pp. 1-4) See abstract; p. 1, left colunm, the last paragraph—right column first paragraph, the last paragraph; p. 2 left column. first paragraph.

Zhang et al., "Understanding the redox effects of amine and hydroxyl groups of p-aminophenol upon the capacitive performance in KOH and H2S04 electrolyte", J Electroanalytical Chemistry, Aug. 16, 2016, vol. 778, pp. 80-86. See abstract; p. 80. left column. second paragraph—right column, lines 1-14 25-28; p. 86 "4 Conclusion" section.

Zhao et al., "Solubilities of p-Aminophenol in Sulfuric Acid + Water + (Methanol, Ethanol, 1-Propanol, 2-Propanol, 1,2-Propanediol, and Glyccerin, Respectively) from (292.35 to 348.10) K", Journal of Chemical and Engineering Data, vol. 51, No. 2, Jan. 25, 2006, XP055597975, pp. 376-381.

Zhao, Yu, et al., "ChemInform Abstract: A Chemistry and Material Perspective on Lithium Redox Flow Batteries Towards High-Density Electrical Energy Storage," Chemical Society Reviews, vol. 44, No. 22, Nov. 21, 2015, pp. 7968-7996, doi:10.1002/chin.201550239 (Year 2015).

* cited by examiner

[Figure 1]
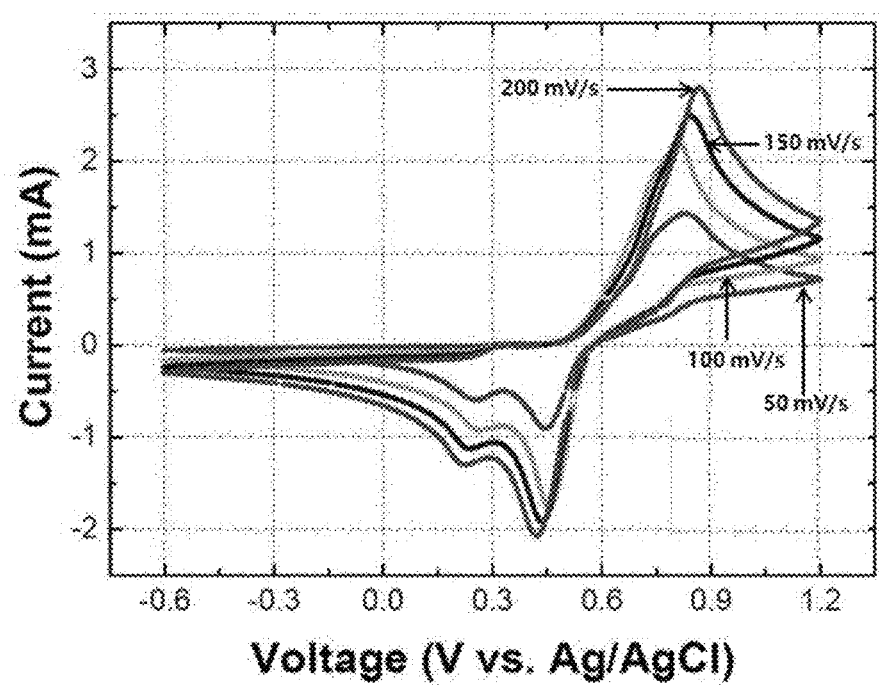
[Figure 2]
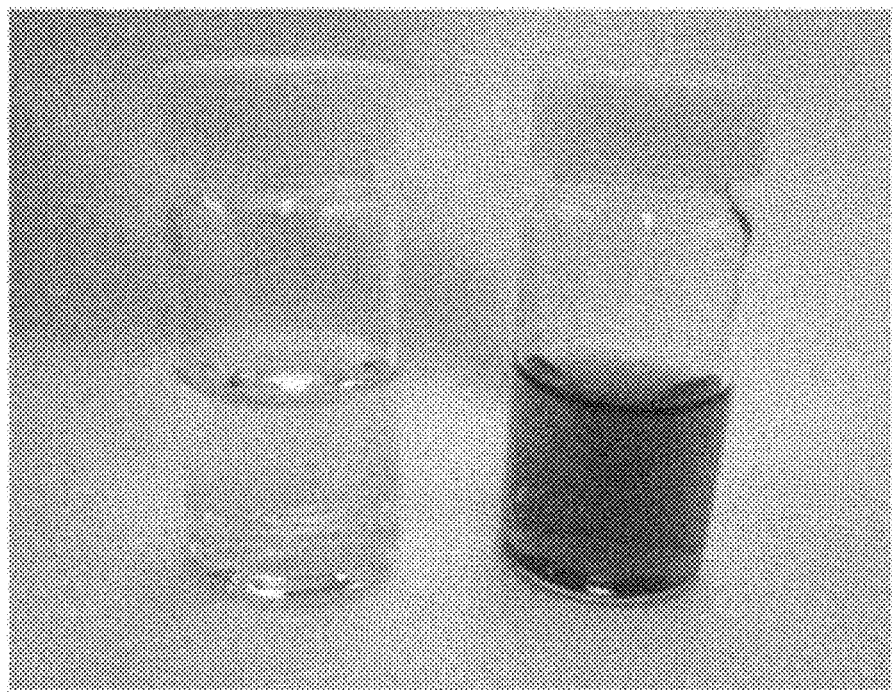

[Figure 3]
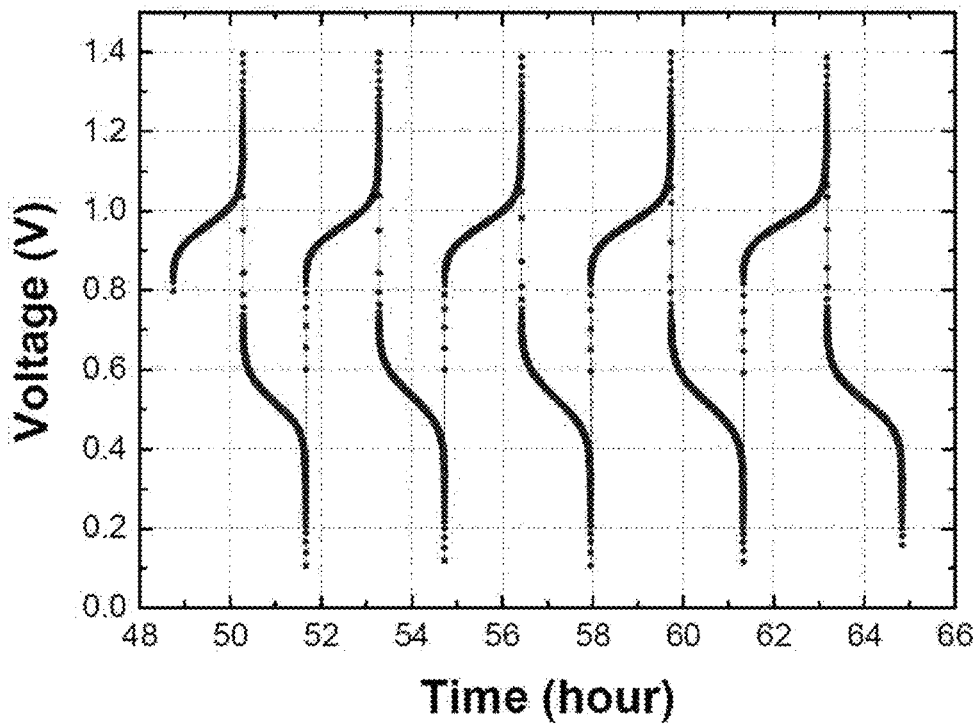
[Figure 4]
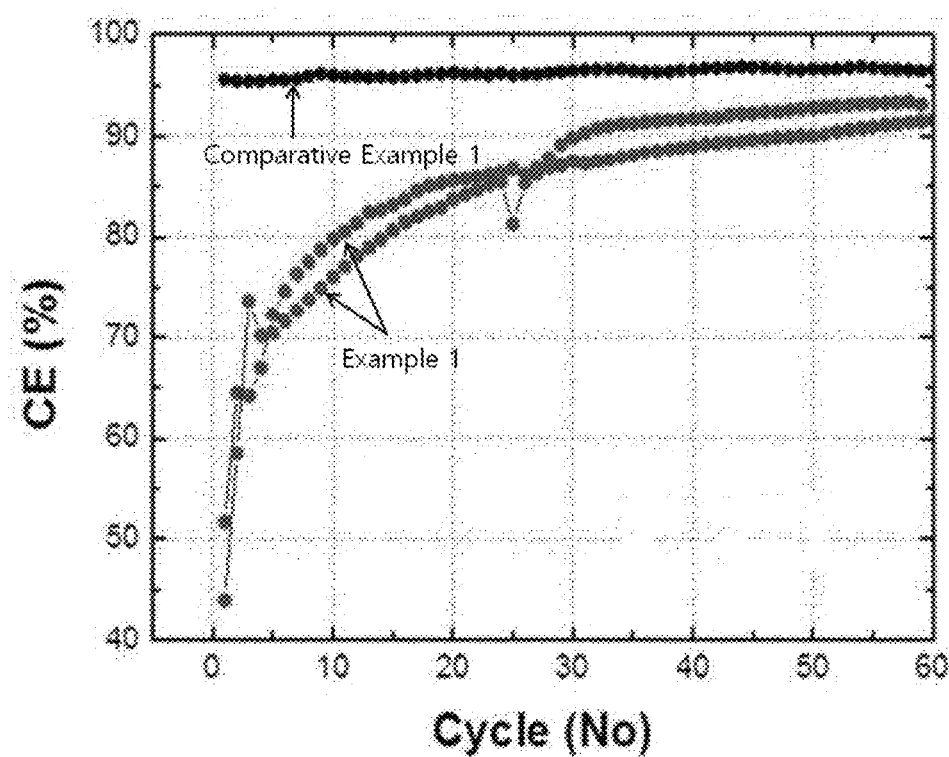

ORGANIC POSITIVE ELECTRODE ACTIVE MATERIAL FOR AQUEOUS REDOX FLOW BATTERY

This application is a Divisional of copending application Ser. No. 16/308,092 filed on Dec. 7, 2018, which is the U.S. National Phase of PCT/KR2017/010427, filed Sep. 22, 2017, and which claims priority under 35 U.S.C. § 119(a) to Korean Application No. 10-2016-0121644, filed on Sep. 22, 2016, the disclosure of which is incorporated herein by reference in its entirety.

TECHNICAL FIELD

The present invention relates to an organic positive electrode active material for aqueous redox flow batteries, and more particularly, to technology of applying an organic positive electrode active material to make up for the drawbacks of conventional aqueous redox flow batteries.

BACKGROUND ART

Redox flow batteries have come into the spotlight as secondary batteries having economic feasibility and a long lifespan. Unlike conventional secondary batteries using lithium and sodium, the redox flow batteries have a capacity expression mechanism in which the battery is charged and discharged through an oxidation-reduction reaction of each of active materials in positive and negative electrodes in a state in which each of the active materials is dissolved in a solvent. Because the redox flow battery is a secondary battery in which the active materials of the electrodes are dissolved in a solvent to react in this way, a change in a standard reduction potential of a redox couple of the active materials dissolved in electrolytes used as the negative and positive electrode electrolytes causes a difference in potential between the active materials to determine a working voltage of a cell.

Also, because a capacity of the redox flow battery is expressed in response to a redox reaction of an electrolyte supplied from an external tank, the redox flow battery has an advantage in that the entire capacity of a cell may be easily controlled by adjusting the size of an external storage tank. Further, because a redox reaction of active materials as a redox couple occurs on surface of positive and negative electrodes, the redox flow battery has an advantage in that the battery exhibits superior lifespan characteristics since the electrodes are less deteriorated, compared to conventional batteries (e.g., lithium ion batteries) in which ions are inserted/eliminated into/from an electrode active material. Vanadium-based salts and water have been widely used as the active materials and the solvent used in the redox flow batteries, respectively. One representative example of such a redox flow battery is an all-vanadium-based redox flow battery. In this case, a vanadium salt is dissolved and used in the positive and negative electrode electrolytes.

The redox flow battery has another important feature that a medium/large energy storage system is not affected by ambient environments, that is, a temperature, and the like. Considering these facts, there is a need for improvement in conventional aqueous systems. Because all-vanadium-based batteries use water as a solvent, the batteries have several problems. First, when a cell is driven at a potential of 1.23 V or higher, the value of which is referred to as an electrochemical stability window of water, an electrolyte is lost due to decomposition of the solvent. As a result, aqueous redox flow batteries have limitations in terms of a working voltage.

Next, because it is difficult to drive an aqueous redox flow battery at a temperature of 0° C. or less due to the thermodynamic characteristics of water, the aqueous redox flow battery has limitations in environments in which the battery is used. Further, there are problems caused by the active materials of the all-vanadium battery. For example, the problems are caused because a positive electrode active material precipitates at a high temperature. M. Skyllas-Kazacos, *JOURNAL OF APPLIED ELECTROCHEMISTRY*, 20, 463-467 (1990) reported that pentavalent vanadium ions precipitate in the form of vanadium penoxide ($V_2O_5$) at a temperature of approximately 40° C. in case of an active material for all-vanadium-based redox flow batteries as an sulfuric acid-based active material most widely known in the art. Owing to these characteristics, the sulfuric acid-based electrolyte for all-vanadium redox flow batteries has a problem in that a solute density directly related to the capacity decreases due to such precipitation. For application to medium/large electric power storage systems whose high capacity, long lifespan, and high stability are considered to be of importance, a low working voltage and a narrow temperature range for use have been pointed out as the serious drawbacks of the all-vanadium redox flow batteries.

PRIOR-ART DOCUMENT

[Patent Document]
Korean Patent Publication No. 10-2016-0035338 "Redox Flow Battery Comprising All Organic Redox Couple as Active Material"

DISCLOSURE

Technical Problem

When a conventional redox flow battery uses an aqueous-based electrolyte as described above, the conventional redox flow battery has limitations in an increase in concentration of an active material, and has a drawback in that a metal is deposited when the active material is used at a high concentration. Particularly, the all-vanadium-based redox flow battery has a problem in that vanadium is deposited in the form of a metal during a redox reaction while the battery is being operated.

Therefore, the present invention is designed to solve the problems of the prior art, and it is an object of the present invention to provide an electrolyte for redox flow batteries having no problems regarding metal deposition because an organic active material is used as an active material and also capable of enhancing solubility to promote improvement of energy density and attaining a high working voltage as well.

Technical Solution

According to an object of the present invention, there is provided an organic positive electrode active material for aqueous redox flow batteries, which includes a compound represented by the following Formula 1:

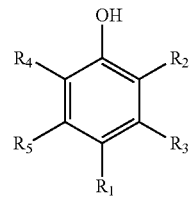

[Formula 1]

wherein $R_1$ to $R_5$ are the same or different from each other, and each independently represent H, $NH_2$, $NO_2$, X, $CX_3$, or CN, and X is a halogen element, provided that at least one of $R_1$ to $R_5$ is not H.

In addition, there is provided a redox flow battery which is charged/discharged, which includes a positive electrode cell including a positive electrode and a positive electrode electrolyte; a negative electrode cell including a negative electrode and a negative electrode electrolyte; an ion exchange membrane disposed between the positive electrode cell and the negative electrode cell; and a positive electrode electrolyte tank configured to supply a positive electrode electrolyte to the positive electrode cell by driving a pump and having a positive electrode electrolyte stored therein and a negative electrode electrolyte tank configured to supply a negative electrode electrolyte to the negative electrode cell by driving a pump and having a negative electrode electrolyte stored therein, wherein each of the positive electrode electrolyte and the negative electrode electrolyte includes an electrode active material and an aqueous solvent. In this case, the positive electrode active material included in the positive electrode electrolyte is the compound represented by Formula 1.

Advantageous Effects

The aqueous redox flow battery to which the positive electrode active material of the present invention is applied has no problems regarding metal deposition, and can also be useful in realizing a high energy density because the active material may be used at high concentration due to an increase in solubility in a solvent, attaining a high working voltage, and enhancing energy efficiency. Also, the aqueous redox flow battery has excellent economic feasibility because an expensive organic electrolyte is not used.

DESCRIPTION OF DRAWINGS

FIG. 1 is data obtained from a cyclic voltammetry test on a single cell to which a 4-aminophenol aqueous solution according to the present invention is applied as a positive electrode electrolyte.

FIG. 2 is an image of the 4-aminophenol aqueous solution according to the present invention before and after the cyclic voltammetry test.

FIG. 3 is a charge/discharge voltage-time graph of the single cell to which the 4-aminophenol aqueous solution according to the present invention is applied as the positive electrode electrolyte.

FIG. 4 is current efficiency data obtained during a charge/discharge cycle of the single cell to which the 4-aminophenol aqueous solution according to the present invention is applied as the positive electrode electrolyte.

BEST MODE

When a redox flow battery is a vanadium-based redox flow battery in a typical shape, the battery may be charged and discharged by circulating a positive electrode electrolyte, which includes a sulfuric acid electrolyte containing tetravalent vanadium ions ($V^{4+}$) and pentavalent vanadium ions ($V^{5+}$), into a positive electrode cell and circulating a negative electrode electrolyte, which contains trivalent vanadium ions ($V^{3+}$) and bivalent vanadium ions ($V^{2+}$), into a negative electrode cell. In this case, because the vanadium ions release electrons, $V^{4+}$ is oxidized into $V^{5+}$ during a charging cycle in the positive electrode cell, and $V^{3+}$ is reduced into $V^{2+}$ by the electrons returned through an outside line in the negative electrode cell.

However, pentavalent vanadium ions in the positive electrode electrolyte generated in the positive electrode precipitate in the form of $V_2O_5$ at a temperature of approximately 40° C. or higher. In this case, the resulting precipitates have a problem in that the precipitates are not re-dissolved in an electrolyte.

To solve the above problems, the present invention provides an organic positive electrode active material for aqueous redox flow batteries, which includes a compound represented by the following Formula 1, in order to replace vanadium used as a conventional positive electrode active material.

[Formula 1]

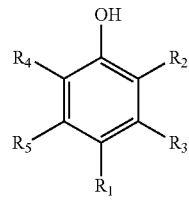

wherein $R_1$ to $R_5$ are the same or different from each other, and each independently represent H, $NH_2$, $NO_2$, X, $CX_3$, or CN, and X is a halogen element, provided that at least one of $R_1$ to $R_5$ is not H.

Preferably, in the compound represented by Formula 1, $R_1$ is an electron-donating group, that is, an $NH_2$ functional group, or an electron-withdrawing group, that is, $NO_2$ or a halogen (F, Cl, Br, or I), and $R_2$ to $R_5$ are H. For example, the organic positive electrode active material for aqueous redox flow batteries provided in the present invention may be para-aminophenol represented by the following Formula 2, or nitrophenol represented by the following Formula 3. The compound of the following Formula 2 or 3 is in a redox state as shown herein, and may be applied under an aqueous electrolyte environment in an aqueous solution state because the compound has a characteristic of being highly soluble in water.

[Formula 2]

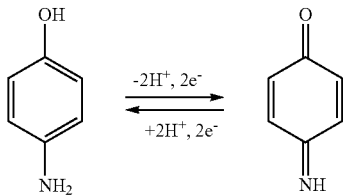

[Formula 3]

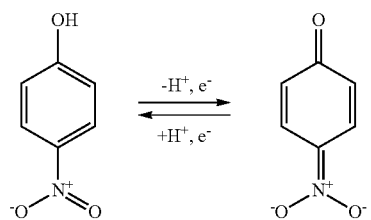

As described above, the compound represented by Formula 1 (including the compounds of Formulas 2 and 3) used as the positive electrode active material may be used at a concentration of 0.01 to 5 M, more preferably a concentration of 0.1 to 2 M in the electrolyte. When the compound is used within this range, excellent energy efficiency may be achieved.

According to the present invention, the positive electrode electrolyte includes the aforementioned positive electrode active material and an aqueous solvent. An aqueous solution including at least one selected from sulfate ions ($SO_4^{2-}$), phosphate ions ($PO_4^{3-}$), and nitrate ions ($NO_3^-$) may be suitably used as the aqueous solvent. Such aqueous acid solutions may have a plurality of effects of promoting improvement of stability or reactivity of the positive electrode active material ions in the electrolyte and improvements of solubility, reducing internal resistance of the battery due to high ionic conductivity, and preventing generation of chlorine gas ($Cl_2$) unlike the use of hydrochloric acid (HCl). Preferably, the aqueous solvent includes one or more selected from the group consisting of $H_2SO_4$, $K_2SO_4$, $Na_2SO_4$, $H_3PO_4$, $H_4P_2O_7$, $K_2HPO_4$, $Na_3PO_4$, $K_3PO_4$, $HNO_3$, $KNO_3$, $NaNO_3$, and a combination thereof.

According to one exemplary embodiment of the present invention, the solvent used in the positive electrode electrolyte and the negative electrode electrolyte may be in the form of an aqueous $H_2SO_4$ solution. When an aqueous sulfuric acid ($H_2SO_4$) solution is used as the solvent for the electrolyte as described above, improvements of stability and reactivity of the positive electrode active material, a decrease in internal resistance, and the like may be promoted, as described above. In this case, when the concentration of sulfuric acid is excessively high, the presence of sulfate ions may cause a decline in solubility of the positive electrode active material or an increase in viscosity of the electrolyte. Therefore, the concentration of sulfuric acid is preferably less than or equal to 5 M, more preferably in a range of 1 to 3 M.

As described above, when the positive and negative electrode electrolytes of the redox flow battery include the aforementioned electrolyte according to the present invention, the redox flow battery has no problems regarding metal deposition because the organic compound represented by Formula 1 is used as the active material, and may also be useful in realizing a high energy density because the active material may be used at high concentration due to an increase in solubility in the solvent, and attaining a high working voltage when the active material is applied to redox flow batteries.

Also, the present invention provides a redox flow battery which is charged/discharged, which includes: a positive electrode cell including a positive electrode and a positive electrode electrolyte; a negative electrode cell including a negative electrode and a negative electrode electrolyte; an ion exchange membrane disposed between the positive electrode cell and the negative electrode cell; and a positive electrode electrolyte tank configured to supply a positive electrode electrolyte to the positive electrode cell by driving a pump and having a positive electrode electrolyte stored therein and a negative electrode electrolyte tank configured to supply a negative electrode electrolyte to the negative electrode cell by driving a pump and having a negative electrode electrolyte stored therein.

In this case, each of the positive electrode electrolyte and the negative electrode electrolyte includes an electrode active material and an aqueous solvent. Here, the positive electrode active material included in the positive electrode electrolyte is the compound represented by Formula 1.

Also, the negative electrode electrolyte may contain positive bivalent vanadium ions ($V^{2+}$) and positive trivalent vanadium ions ($V^{3+}$). To generate such vanadium ions, the negative electrode electrolyte may include a vanadium salt, and the vanadium salt is not particularly limited as long as the vanadium salt can release vanadium ions. For example, the vanadium salt may include vanadium sulfate, vanadium acetylacetonate, vanadium oxide sulfate hydrate, vanadium oxytriethoxide, and vanadium oxyfluoride. Preferably, vanadium sulfate is used in consideration of solubility. For example, tetravalent positive ions ($VO^{2+}=V^{4+}$) of the electrolyte in which a vanadium salt such as vanadium sulfate ($VOSO_4$) is dissolved may be electrically reduced into trivalent positive ions ($V^{3+}$), which may be then used.

According to the present invention, the negative electrode electrolyte includes the aforementioned vanadium salt and an aqueous solvent. For the same reason as in the aforementioned positive electrode electrolyte, the aqueous solvent preferably includes one or more selected from $H_2SO_4$, $K_2SO_4$, $Na_2SO_4$, $H_3PO_4$, $H_4P_2O_7$, $K_2HPO_4$, $Na_3PO_4$, $K_3PO_4$, $HNO_3$, $KNO_3$, $NaNO_3$, HCl, and a combination thereof.

Ion exchange membranes used in the conventional redox flow batteries may be used as the ion exchange membrane without any limitation. For example, the ion exchange membrane may be a fluorine-based polymer, a partial fluorine-based polymer, or a hydrocarbon-based polymer. More specifically, the ion exchange membrane may be selected from a homocopolymer, an alternating copolymer, a random copolymer, a block copolymer, a multiblock copolymer or a grafting copolymer. In this case, these copolymers are composed of one or more polymers selected from the group consisting of a perfluorosulfonic acid-based polymer, a hydrocarbon-based polymer, an aromatic sulfone-based polymer, an aromatic ketone-based polymer, a polybenzimidazole-based polymer, a polystyrene-based polymer, a polyester-based polymer, a polyimide-based polymer, a polyvinylidene fluoride-based polymer, a polyethersulfone-based polymer, a polyphenylene sulfide-based polymer, a polyphenylene oxide-based polymer, a polyphosphagen-based polymer, a polyethylene naphthalate-based polymer, a polyester-based polymer, a doped polybenzimidazole-based polymer, a polyether ketone-based polymer, a polyphenyl quinoxaline-based polymer, a polysulfone-based polymer, a sulfonated polyarylene ether-based polymer, a sulfonated polyether ketone-based polymer, a sulfonated polyether ether ketone-based polymer, a sulfonated polyamide-based polymer, a sulfonated polyimide-based polymer, a sulfonated polyphosphagen-based polymer, a sulfonated polystyrene-based polymer, and a radiation-polymerized sulfonated low-density polyethylene-g-polystyrene-based polymer.

MODE FOR INVENTION

Hereinafter, preferred exemplary embodiments of the present invention will be described in order to aid in understanding the present invention. However, it should be understood that the description proposed herein is just a preferable example for the purpose of illustrations only. Therefore, it will be apparent to those skilled in the art that various changes and modifications can be made to the exemplary embodiments of the present invention without departing from the scope of the present invention, so it should be understood that the present invention covers all such changes and modifications provided they are within the scope of the appended claims and their equivalents.

Preparative Example 1

0.4 M 4-aminophenol was dissolved in an aqueous 3.0 M $H_2SO_4$ solution to prepare a positive electrode electrolyte.

Experimental Example 1

To check redox characteristics of the positive electrode electrolyte prepared in Example 1, cyclic voltammetry was carried out using glassy carbon, Ag/AgCl and a platinum (Pt) wire as a working electrode, a reference electrode, and a counter electrode, respectively. Current values measured at a working electrode when a voltage spanning from −0.6 to 1.2 V was applied to the working electrode with a varying scan rate of 50 to 200 mV/s were recorded. The results are shown in FIG. 1.

Results

Referring to FIG. 1, from the results evaluated by the cyclic voltammetry, it can be seen that an oxidation/reduction current peak value increases as the scan rate increases, and this was a $2e^-$ reaction because two peaks were observed during a reduction process. These results suggested that a reversible redox reaction was possible in an acidic aqueous solution.

Also, FIG. 2 is an image of the 4-aminophenol aqueous solution before and after the cyclic voltammetry test. It was confirmed that the aqueous solution turned into purple during charging.

Example 1

Positive and negative electrodes were manufactured using carbon felt with a size of 5×5 cm$^2$, a bipolar plate, and a gold current collector. In this case, Nafion 115 was used as the ion exchange membrane.

The electrolyte prepared in Preparative Example 1 was used as the positive electrode electrolyte. For the negative electrode electrolyte, 1.0 M vanadium sulfate (VOSO$_4$) was dissolved in an aqueous 3.0 M sulfuric acid solution (H$_2$SO$_4$) to prepare a tetravalent vanadium (VO$^{2+}$) solution, and the solution was electrically reduced to form trivalent vanadium ions (V$^{3+}$), which was then used.

A redox flow battery was manufactured using the battery thus assembled, the negative electrode electrolyte, and the positive electrode electrolyte prepared in Example 1. In this case, the electrolyte was circulated at a rate of 25 cc/min using a pump.

Comparative Example 1

A redox flow battery was manufactured in the same manner as in Example 1, except that the positive electrode electrolyte was prepared by dissolving 1.0 M VOSO$_4$ in an aqueous 3.0 M H$_2$SO$_4$ solution, and trivalent vanadium ions (V$^{3+}$) obtained by separating ions from the positive electrode electrolyte were used as the negative electrode electrolyte. Thereafter, the electrolyte was circulated.

Experimental Example 2

To evaluate the charge/discharge characteristics of the redox flow battery manufactured in Example 1, the redox flow battery was charged and discharged at ±100 mA in a voltage range of 0.1 to 1.4 V, and charge/discharge voltages with time are shown in FIG. 3.

Results

FIG. 3 is a graph illustrating a change in voltage for 16$^{th}$ to 20$^{th}$ charge/discharge cycles from the beginning. It was revealed that the redox flow battery was rechargeable and re-dischargeable within the same period of time at the same voltage as previously even when the number of charge/discharge cycles increased. That is, it can be seen that the redox reaction of the electrolyte on surfaces of the electrodes was reversible. Therefore, it can be seen that the charge/discharge behaviors of the single cell using 4-aminophenol as the positive electrode electrolyte were determined, and a working voltage range of the single cell was confirmed.

Experimental Example 3

Expression capacities and current efficiencies of the redox flow batteries manufactured in Example 1 and Comparative Example 1 were measured. The current efficiency is an index that represents a degree of reversibility of a battery as a ratio of the quantity of discharged charges to the quantity of charged charges, and means that the battery is stably charged and discharged without an irreversible change of a material so that the current efficiency reaches 100%. Therefore, the efficiency represents an important value evaluated for the battery, the value of which may indirectly represent the lifespan of the battery. Together with the expression capacities, the results are listed in Table 1 and shown in FIG. 4. In this case, the redox flow batteries of Example 1 and Comparative Example 1 were assembled to having the same materials and areas, but were driven in different working voltage ranges of 0.4 to 1.2 V and 0.8 to 1.7 V, respectively, due to a difference in electrolytes therebetween.

TABLE 1

| | Current efficiency (60$^{th}$ cycle, %) | |
|---|---|---|
| | Measured once | Measured in duplicate |
| Example 1 | 91.6 | 93.1 |
| Comparative Example 1 | 96.2 | 97.0 |

Results

As can be seen from the results of Table 1 and FIG. 4, it was revealed that the current efficiencies of the redox flow battery of Example 1 were measured to be 91.6 and 93.1, which were compared to the current efficiencies (96.2 and 97.0) of the vanadium redox flow battery of Comparative Example 1. Therefore, it was confirmed that the positive electrode electrolyte of Example 1 can be replaced with the positive electrode electrolyte for conventional vanadium batteries.

The invention claimed is:

1. A redox flow battery which is charged/discharged, comprising:
   a positive electrode cell comprising a positive electrode and a positive electrode electrolyte;
   a negative electrode cell comprising a negative electrode and a negative electrode electrolyte;
   an ion exchange membrane disposed between the positive electrode cell and the negative electrode cell; and
   a positive electrode electrolyte tank configured to supply the positive electrode electrolyte to the positive electrode cell by driving a pump and having the positive electrode electrolyte stored therein
   and a negative electrode electrolyte tank configured to supply the negative electrode electrolyte to the negative electrode cell by driving a pump and having the negative electrode electrolyte stored therein,
   wherein each of the positive electrode electrolyte and the negative electrode electrolyte comprises
   an electrode active material and an aqueous solvent,
   wherein the positive electrode active material included in the positive electrode electrolyte comprises a compound represented by the following Formula 1, and does not comprise vanadium ions, and
wherein the negative electrode electrolyte contains positive bivalent vanadium ions ($V^{2+}$) and positive trivalent vanadium ions ($V^{3+}$):

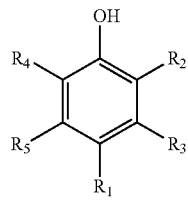

[Formula 1]

wherein $R_1$ is $NH_2$, and $R_2$ to $R_5$ are H.

2. The redox flow battery of claim 1, wherein the positive electrode active material is included at a concentration of 0.01 to 5 M.

3. The redox flow battery of claim 2, wherein the aqueous solvent of the positive electrode electrolyte comprises one or more selected from the group consisting of $H_2SO_4$, $K_2SO_4$, $Na_2SO_4$, $H_3PO_4$, $H_4P_2O_7$, $K_2HPO_4$, $Na_3PO_4$, $K_3PO_4$, $HNO_3$, $KNO_3$, $NaNO_3$, and a combination thereof.

* * * * *